US012427268B2

(12) United States Patent
Prechtel

(10) Patent No.: US 12,427,268 B2
(45) Date of Patent: Sep. 30, 2025

(54) ACCESS NEEDLE INDICATION SYSTEMS FOR LOCATING AND ACCESSING SUBCUTANEOUS MEDICAL DEVICES

(71) Applicant: Bard Peripheral Vascular, Inc., Franklin Lakes, NJ (US)

(72) Inventor: Ericka J. Prechtel, Salt Lake City, UT (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 176 days.

(21) Appl. No.: 18/036,359

(22) PCT Filed: Nov. 24, 2020

(86) PCT No.: PCT/US2020/062076
§ 371 (c)(1),
(2) Date: May 10, 2023

(87) PCT Pub. No.: WO2022/115099
PCT Pub. Date: Jun. 2, 2022

(65) Prior Publication Data
US 2024/0009407 A1 Jan. 11, 2024

(51) Int. Cl.
*A61M 39/02* (2006.01)
*A61M 5/42* (2006.01)
(52) U.S. Cl.
CPC ........ *A61M 5/427* (2013.01); *A61M 39/0208* (2013.01); *A61M 2205/3317* (2013.01);
(Continued)
(58) Field of Classification Search
CPC .................... A61M 5/427; A61M 39/0208
See application file for complete search history.

(56) References Cited

U.S. PATENT DOCUMENTS 5,061,248 A 10/1991 Sacco
5,342,311 A 8/1994 Dirina
(Continued)

FOREIGN PATENT DOCUMENTS

CN 1878591 A 12/2006
CN 1899222 A 1/2007
(Continued)

OTHER PUBLICATIONS

CN 201180033387.5 filed Jan. 5, 2013 First Office Action dated Oct. 16, 2014.
(Continued)

*Primary Examiner* — Rochelle D Turchen
(74) *Attorney, Agent, or Firm* — Rutan & Tucker LLP

(57) ABSTRACT

Embodiments disclosed herein are directed to access devices configured to access a subcutaneous medical device. The access device can include a needle supported by a needle hub and in some embodiments a housing slidably engaged therewith and configured to align the needle axis at a predetermined angle. The access device can include an indicator system configured to detect when the needle is correctly aligned with a target window of a port. This can allow for smaller, lower profile ports with smaller target windows while mitigating mis sticks. The indicator system can be contained within the access device little or no increase to the overall size of the access device. The indicator system can employ various modalities including capacitance, induction, magnetic, thermal, acoustic, or radio frequency (RF).

8 Claims, 6 Drawing Sheets

(52) U.S. Cl.
CPC .............. *A61M 2205/3375* (2013.01); *A61M 2205/583* (2013.01)

(56) References Cited

U.S. PATENT DOCUMENTS

| | | | |
|---|---|---|---|
| 5,360,407 A | 11/1994 | Leonard et al. | |
| 5,423,334 A | 6/1995 | Jordan | |
| 5,460,612 A | 10/1995 | Madore | |
| 5,476,460 A | 12/1995 | Montalvo | |
| 5,533,979 A | 7/1996 | Nabai et al. | |
| 5,620,419 A | 4/1997 | Lui et al. | |
| 5,758,667 A | 6/1998 | Slettenmark | |
| 5,771,895 A | 6/1998 | Slager | |
| 5,797,954 A | 8/1998 | Shaffer et al. | |
| 6,654,629 B2 | 11/2003 | Montegrande | |
| 6,673,091 B1 | 1/2004 | Shaffer et al. | |
| 7,044,932 B2 | 5/2006 | Borchard et al. | |
| 7,329,239 B2 | 2/2008 | Safabash et al. | |
| 7,621,749 B2 | 11/2009 | Munday | |
| 7,632,263 B2 | 12/2009 | Denoth et al. | |
| 7,708,730 B2 | 5/2010 | Steinbach et al. | |
| 7,762,993 B2 | 7/2010 | Perez | |
| 7,794,451 B1 | 9/2010 | Chuter et al. | |
| 7,824,371 B2 | 11/2010 | Perez | |
| 7,914,510 B2 | 3/2011 | Steinbach et al. | |
| 8,171,938 B2 | 5/2012 | Bengtson | |
| 8,177,808 B2 | 5/2012 | Mullani | |
| 8,192,398 B2 | 6/2012 | Hoendervoogt et al. | |
| 8,246,578 B2 | 8/2012 | Matsumoto | |
| 8,308,740 B2 | 11/2012 | Tolley et al. | |
| 8,475,407 B2 | 7/2013 | Kalpin et al. | |
| 8,534,293 B2 | 9/2013 | Bzostek et al. | |
| RE44,639 E | 12/2013 | Squitieri | |
| 8,715,232 B2 | 5/2014 | Yodfat et al. | |
| 8,795,229 B2 | 8/2014 | Bakhtyari-Nejad-Esfahani | |
| 8,894,616 B2 | 11/2014 | Harrison et al. | |
| 8,926,591 B2 | 1/2015 | Schutz et al. | |
| 8,974,422 B2 | 3/2015 | Gill et al. | |
| 9,884,150 B2 | 2/2018 | Jho et al. | |
| 10,420,884 B2 | 9/2019 | Howell et al. | |
| 10,471,205 B2 | 11/2019 | Jho et al. | |
| 2002/0022855 A1 | 2/2002 | Bobroff et al. | |
| 2002/0067359 A1 | 6/2002 | Brodsky et al. | |
| 2002/0072720 A1 | 6/2002 | Hague et al. | |
| 2003/0040753 A1 | 2/2003 | Daum et al. | |
| 2003/0163096 A1 | 8/2003 | Swenson et al. | |
| 2003/0204165 A1 | 10/2003 | Houben et al. | |
| 2005/0059884 A1 | 3/2005 | Krag | |
| 2005/0101912 A1 | 5/2005 | Faust et al. | |
| 2005/0119611 A1 | 6/2005 | Marano-Ford et al. | |
| 2005/0154303 A1 | 7/2005 | Walker et al. | |
| 2006/0033609 A1 | 2/2006 | Bridgelall | |
| 2006/0247584 A1 | 11/2006 | Sheetz et al. | |
| 2006/0264898 A1 | 11/2006 | Beasley et al. | |
| 2007/0078391 A1 | 4/2007 | Wortley et al. | |
| 2007/0191772 A1 | 8/2007 | Wojcik | |
| 2007/0238984 A1 | 10/2007 | Maschke et al. | |
| 2007/0282196 A1 | 12/2007 | Birk et al. | |
| 2008/0004642 A1 | 1/2008 | Birk et al. | |
| 2008/0021313 A1 | 1/2008 | Eidenschink et al. | |
| 2008/0083413 A1 | 4/2008 | Forsell | |
| 2008/0319414 A1 | 12/2008 | Yodfat et al. | |
| 2009/0062744 A1 | 3/2009 | Weilbacher et al. | |
| 2009/0082782 A1 | 3/2009 | Kalpin | |
| 2009/0093765 A1 | 4/2009 | Glenn | |
| 2009/0105688 A1 | 4/2009 | McIntyre et al. | |
| 2009/0156928 A1 | 6/2009 | Evans et al. | |
| 2009/0227951 A1 | 9/2009 | Powers et al. | |
| 2010/0004597 A1 | 1/2010 | Gyrn et al. | |
| 2010/0010339 A1 | 1/2010 | Smith et al. | |
| 2010/0141454 A1 | 6/2010 | Bantin | |
| 2010/0204765 A1 | 8/2010 | Hall et al. | |
| 2010/0256594 A1 | 10/2010 | Kimmell et al. | |
| 2010/0298704 A1 | 11/2010 | Pelissier et al. | |
| 2011/0237935 A1 | 9/2011 | Kalpin et al. | |
| 2011/0275930 A1 | 11/2011 | Jho et al. | |
| 2012/0172711 A1 | 7/2012 | Kerr et al. | |
| 2012/0289819 A1 | 11/2012 | Snow | |
| 2013/0218085 A1 | 8/2013 | Knobloch | |
| 2014/0039452 A1 | 2/2014 | Bangera et al. | |
| 2014/0097303 A1 | 4/2014 | Lake | |
| 2014/0207110 A1 | 7/2014 | Jonas | |
| 2015/0250944 A1 | 9/2015 | Howell et al. | |
| 2017/0100598 A1 | 4/2017 | Gross et al. | |
| 2018/0154075 A1 | 6/2018 | Jho et al. | |
| 2019/0029760 A1 | 1/2019 | Nahman et al. | |
| 2019/0329015 A1 | 10/2019 | Kang | |
| 2019/0350672 A1 | 11/2019 | Smith et al. | |
| 2019/0351136 A1 | 11/2019 | Howell et al. | |
| 2020/0061288 A1 | 2/2020 | Jho et al. | |
| 2020/0069929 A1* | 3/2020 | Mason | A61M 1/3656 |
| 2020/0368513 A1 | 11/2020 | Amin | |
| 2021/0402085 A1 | 12/2021 | Howell et al. | |

FOREIGN PATENT DOCUMENTS

| | | |
|---|---|---|
| CN | 101066480 A | 11/2007 |
| CN | 101500626 A | 8/2009 |
| CN | 101815550 A | 8/2010 |
| CN | 103327902 A | 9/2013 |
| IN | 103328021 A | 9/2013 |
| JP | H6-296633 A | 10/1994 |
| JP | 2004-283289 A | 10/2004 |
| JP | 2006-102360 A | 4/2006 |
| JP | 2008-539025 A | 11/2008 |
| JP | 2013-531999 | 8/2013 |
| WO | 2006101993 A2 | 9/2006 |
| WO | 2006116438 A2 | 11/2006 |
| WO | 2010015001 A1 | 2/2010 |
| WO | 2011140379 A2 | 11/2011 |
| WO | 2012034085 A1 | 3/2012 |
| WO | 2013152209 A1 | 10/2013 |
| WO | 2014155075 A1 | 10/2014 |
| WO | 2015134766 A1 | 9/2015 |
| WO | 2019147857 A1 | 8/2019 |
| WO | 2022115099 A1 | 6/2022 |

OTHER PUBLICATIONS

CN 201180033387.5 filed Jan. 5, 2013 Second Office Action dated Apr. 13, 2015.
CN 201180033387.5 filed Jan. 5, 2013 Third Office Action dated Sep. 2, 2015.
CN 201580012524.5 filed Sep. 7, 2016 Office Action dated Jan. 21, 2019.
CN 201610592317.8 filed Jul. 25, 2016 Office Action dated Feb. 24, 2018.
CN 201610592317.8 filed Jul. 25, 2016 Office Action dated Nov. 12, 2018.
EP 15757893.1 filed Aug. 30, 2016 Extended European Search Report dated Dec. 21, 2016.
EP 15757893.1 filed Aug. 30, 2016 Office Action dated Feb. 20, 2019.
JP 2013-509275 filed Oct. 30, 2012 Decision of Rejection dated Sep. 2, 2015.
JP 2013-509275 filed Oct. 30, 2012 First Office Action dated Feb. 6, 2015.
JP 2015-249575 filed Dec. 22, 2015 Decision for Rejection dated May 22, 2017.
JP 2015-249575 filed Dec. 22, 2015 First Office Action dated Oct. 4, 2016.
MX/a/2012/012802 filed Nov. 1, 2012 Office Action dated May 31, 2013.
MX/a/2012/012802 filed Nov. 1, 2012 Office Action dated Nov. 19, 2013.
PCT/US2011/035406 filed May 5, 2011 International Preliminary Report on Patentability dated Feburary 20, 2014.
PCT/US2011/035406 filed May 5, 2011 International Seach Report dated Dec. 16, 2011.

(56) References Cited

OTHER PUBLICATIONS

PCT/US2011/035406 filed May 5, 2011 Written Opinion dated Dec. 16, 2011.
PCT/US2015/018999 filed Mar. 5, 2015 Search Report dated Jul. 28, 2015.
PCT/US2019/015013 filed Jan. 24, 2019 International Preliminary Report on Patentability dated Jul. 28, 2020.
PCT/US2019/015013 filed Jan. 24, 2019 International Search Report and Written Opinion dated Jun. 20, 2019.
PCT/US2020/062076 filed Nov. 24, 2020 International Preliminary Report on Patentability dated Apr. 14, 2023.
PCT/US2020/062076 filed Nov. 24, 2020 International Search Report and Written Opinion dated Aug. 11, 2021.
U.S. Appl. No. 13/101,968, filed May 5, 2011 Decision on Appeal dated Jun. 26, 2017.
U.S. Appl. No. 13/101,968, filed May 5, 2011 Final Office Action dated Feb. 6, 2015.
U.S. Appl. No. 13/101,968, filed May 5, 2011 Final Office Action dated Oct. 24, 2013.
U.S. Appl. No. 13/101,968, filed May 5, 2011 Non-Final Office Action dated Apr. 24, 2013.
U.S. Appl. No. 13/101,968, filed May 5, 2011 Non-Final Office Action dated Sep. 11, 2014.
U.S. Appl. No. 13/101,968, filed May 5, 2011 Notice of Allowance dated Sep. 20, 2017.
U.S. Appl. No. 14/639,706, filed Mar. 5, 2015 Final Office Action dated Apr. 27, 2018.
U.S. Appl. No. 14/639,706, filed Mar. 5, 2015 Final Office Action dated Jul. 6, 2017.
U.S. Appl. No. 14/639,706, filed Mar. 5, 2015 Non-Final Office Action dated Dec. 31, 2018.
U.S. Appl. No. 14/639,706, filed Mar. 5, 2015 Non-Final Office Action dated Feb. 17, 2017.
U.S. Appl. No. 14/639,706, filed Mar. 5, 2015 Notice of Allowance dated May 10, 2019.
U.S. Appl. No. 16/961,213, filed Jul. 9, 2020 Non-Final Office Action dated Jun. 1, 2023.
U.S. Appl. No. 15/887,675, filed Feb. 2, 2018 Advisory Action dated Mar. 29, 2019.
U.S. Appl. No. 15/887,675, filed Feb. 2, 2018 Final Office Action dated Jan. 17, 2019.
U.S. Appl. No. 15/887,675, filed Feb. 2, 2018 Non-Final Office Action dated Jun. 14, 2018.
U.S. Appl. No. 15/887,675, filed Feb. 2, 2018 Restriction Requirement dated Apr. 11, 2018.
U.S. Appl. No. 16/672,062, filed Nov. 1, 2019 Board Decision dated May 5, 2022.
U.S. Appl. No. 16/672,062, filed Nov. 1, 2019 Final Office Action dated Jan. 19, 2022.
U.S. Appl. No. 16/672,062, filed Nov. 1, 2019 Non-Final Office Action dated Sep. 20, 2021.
Website: Analog IC Tips, article: How do RFID tags and reader antennas work? https://www.analogictips.com/rfid-tag-and-reader-antennas/ date: May 2, 2017 (Year: 2017).

\* cited by examiner

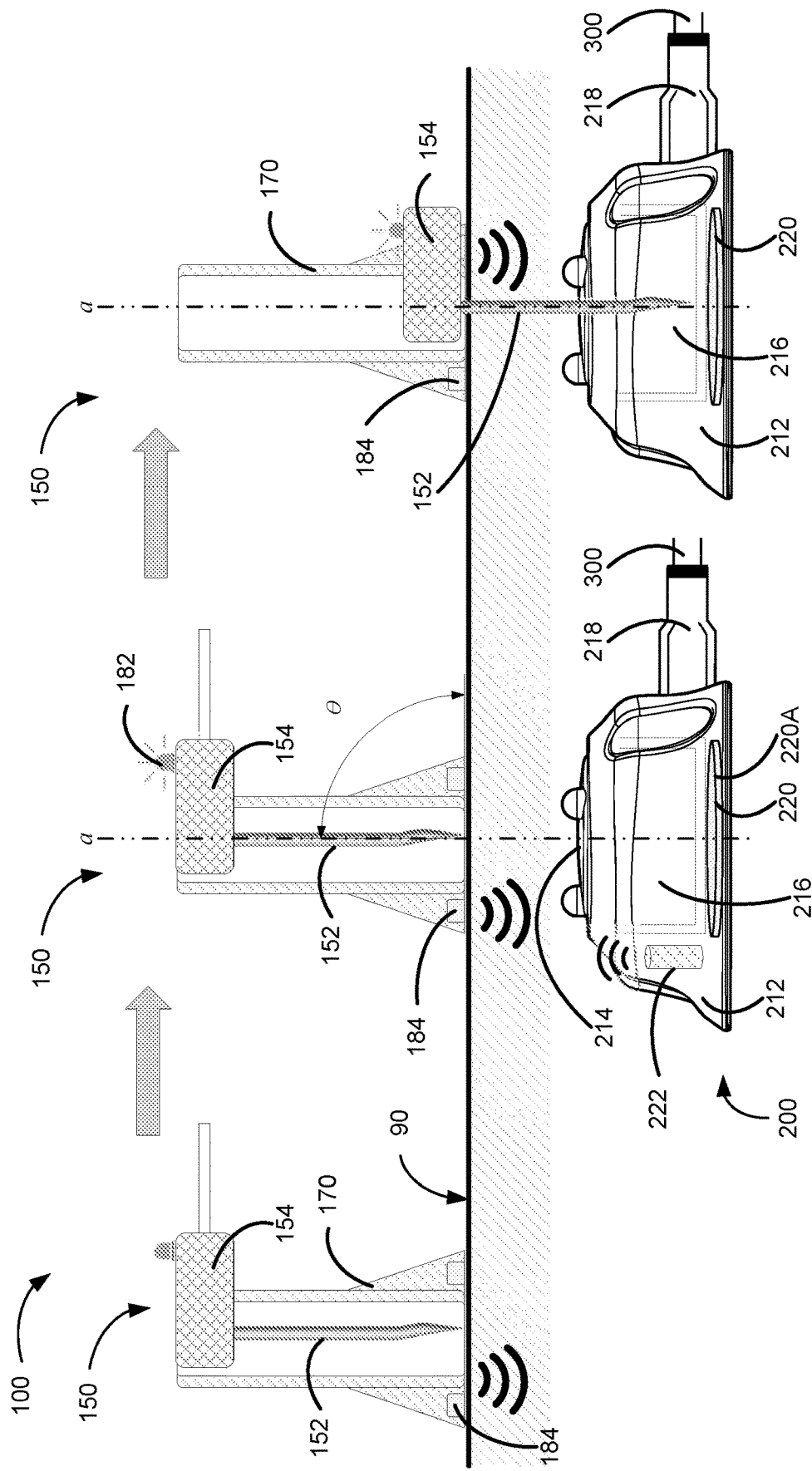

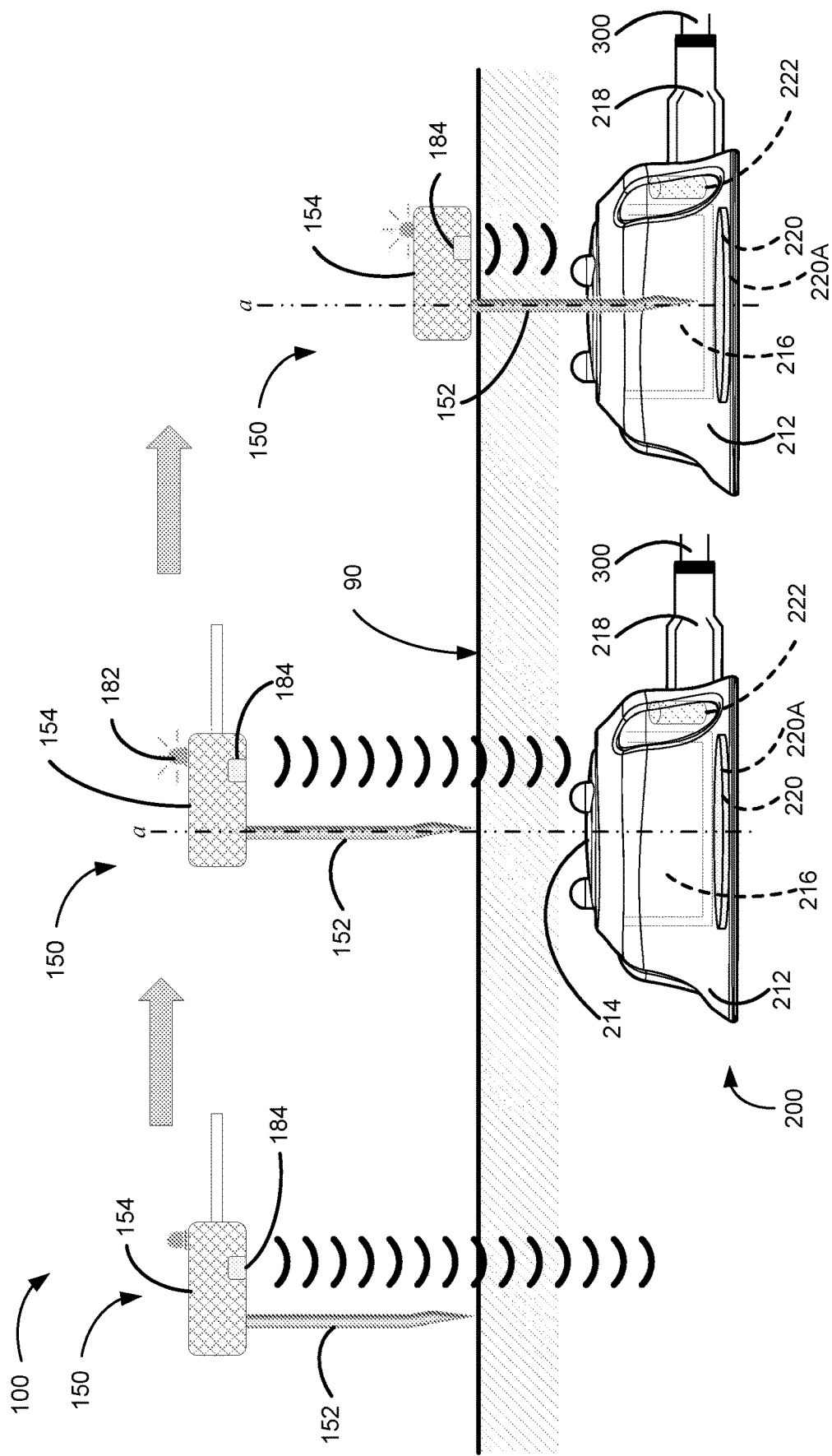

ACCESS NEEDLE INDICATION SYSTEMS FOR LOCATING AND ACCESSING SUBCUTANEOUS MEDICAL DEVICES

This application is a U.S. national stage of International Patent Application No. PCT/US2020/062076, filed Nov. 24, 2020, which is incorporated by reference in its entirety into this application.

BACKGROUND

Subcutaneous medical devices such as "ports" or the like provide a convenient method of repeated vascular access. Ports are implantable within the body and permit the infusion of medicine, parenteral solutions, blood products, or other fluids. Additionally, ports are also used for blood sampling. In common practice, a port is subcutaneously implanted within the body, and a catheter is connected to the port in fluid communication therewith. The catheter is routed to a vasculature where a fluid is desired to be delivered or removed. To deliver the fluid, a caregiver locates a septum of the port by palpation of a patient's skin.

Port access is accomplished by percutaneously inserting a needle, typically a non-coring needle, through the septum of the port and into a reservoir chamber of the port. A fluid containing a drug or some other beneficial substance can then be administered by bolus injection or continuous infusion into the chamber of the port. The fluid then flows through the chamber into the catheter and finally to the remote site where the fluid is desired.

Ports, particularly port septa, are required to be of a certain size in order to be successfully palpated. However, these relatively larger ports can impact wound healing and cause scarring from stretching of the skin. Further, palpating the port and aligning the needle requires experience and training since any slight movement between the palpation of the port and aligning the needle can result in mis-sticks and discomfort for the patient. Smaller or lower profile ports provide improved wound healing, reduced scaring and improved aesthetics, improving the patients overall quality of life. However, these smaller, lower-profile ports and in particular the port septa, are more difficult to locate by palpation and provide an increased risk of mis-sticks.

Disclosed herein are access devices configured to indicate when a needle is correctly aligned with a port and associated methods thereof, allowing for improved needle alignment accuracy and enabling for smaller, lower-profile ports.

SUMMARY

Disclosed herein is an access assembly configured for detecting and accessing a subcutaneous medical device, the access device including, a needle supported by a needle hub, and an indicator system including, a capacitance sensor configured to detect a change in a dielectric constant between the subcutaneous medical device and a surrounding tissue, and an LED light configured to indicate when the needle is aligned with the subcutaneous medical device.

In some embodiments, the access assembly further includes, a housing supporting the needle hub and slidably engaged therewith, the needle hub configured to transition between a retracted position and an extended position, the housing defining a bottom surface configured to engage a skin surface, the sensor disposed in the bottom surface. The LED light is disposed on one of the housing or the needle hub. The subcutaneous medical device is a port including a port body and a septum co-operating to define a reservoir, the needle configured to penetrate the septum to access the reservoir therebelow when the needle is aligned with the subcutaneous medical device. The subcutaneous medical device includes a disc of material that provides an increased difference in dielectric constant from the surrounding tissue. The disc of material includes one of platinum, silver, tungsten, gold, cobalt, titanium, silica, or zirconia. The disc is disposed under the reservoir and defines a diameter that extends the same diameter as the reservoir. The sensor can detect a change in dielectric constant to a depth of between 0.15 inch and 3 inch below the skin surface.

Also disclosed is a vascular access system including, an access device including a needle supported by a needle hub and including a voltmeter sensor and an indicator, and a subcutaneous port device including a port body defining a reservoir and a needle septum disposed thereover, the port body including an induction coil configured to induce a current in the voltmeter sensor to actuate the indicator to provide an alert.

In some embodiments, the induction coil can induce a current within a range of between 0.15 inch and 3 inch and along an axis that extends perpendicular to a skin surface. The alert is one of a visual, audible, or tactile alert. The indicator is an LED bulb that is illuminated by the current from the voltmeter induced by the induction coil. In some embodiments, the vascular access system further includes an integrated circuit or a "555" timer configured to receive a first voltage from the voltmeter and provide a first output to actuate the indicator, and to receive a second voltage from the voltmeter and provide a second output to actuate the indicator.

Also disclosed is a method of accessing a subcutaneous port including, engaging a bottom surface of a housing with a skin surface, the housing slidably engaged with a needle hub that is supporting a needle, the housing aligning an axis of the needle at a predetermined angle relative to the skin surface, detecting a first dielectric constant of a tissue disposed below the bottom surface of the housing, sliding the housing parallel to the skin surface, detecting a second dielectric constant different from the first dielectric constant, actuating an indicator to provide an alert, and sliding a needle hub relative to the housing to penetrate the skin surface with the needle and access the subcutaneous port.

In some embodiments, the alert includes one of a visual, audible, or tactile alert. In some embodiments, actuating the indicator to provide an alert includes illuminating an LED bulb to indicate an axis of the needle is aligned with a reservoir of the subcutaneous port. The bottom surface of the housing includes a capacitance sensor configured to detect a dielectric constant of the tissue disposed below the bottom surface. The subcutaneous port includes a disc of material configured to provide the second dielectric constant. The disc includes one of one of platinum, silver, tungsten, gold, cobalt, titanium, silica, or zirconia. In some embodiments, the method further includes detecting one of the first dielectric constant or the second dielectric constant to a depth of between 0.15 inch and 3 inch below the skin surface. The predetermined angle is less than or equal to 90° relative to the skin surface.

Also disclosed is a method of detecting and accessing a subcutaneous medical device including, providing an access device having a needle extending along an axis and supported by a needle hub, and an indicator system including a voltmeter sensor and an indicator, aligning an axis of the needle with a skin surface at a predetermined angle, sliding the access device parallel to the skin surface, inducing a current in the voltmeter sensor to actuate the indicator, and penetrating the skin surface with the needle to access the subcutaneous medical device.

In some embodiments, the method further includes a housing slidably engaged with the needle hub and including a bottom surface configured to engage the skin surface and align the axis of the needle at the predetermined angle. The voltmeter sensor is disposed in one of the needle hub or the bottom surface of the housing. The predetermined angle is equal to or less than 90° relative to the skin surface. The subcutaneous medical device is a port including an induction coil disposed therein configured to induce a current in the voltmeter sensor. In some embodiments, the method further includes receiving a first voltage from the voltmeter sensor and provide a first output to actuate the indicator, and to receive a second voltage from the voltmeter sensor and provide a second output to actuate the indicator. The first output actuates the indicator at a first rate, and the second output actuates the indicator at a second rate different from the first rate.

Also disclosed is an access system configured for detecting alignment with a subcutaneous medical device, the access system including a needle supported by a needle hub, and an indicator system having an acoustic transducer sensor configured to emit an acoustic signal and detect a first reflected signal, and an LED light disposed on the needle hub configured to indicate when an axis of the needle is aligned with the subcutaneous medical device.

In some embodiments, the access system further includes a housing supporting the needle hub and slidably engaged therewith, the needle hub configured to transition between a retracted position and an extended position, the housing defining a bottom surface configured to engage a skin surface, the acoustic transducer sensor disposed in the bottom surface. The subcutaneous medical device is a port including a port body and a septum co-operating to define a reservoir, the needle configured to penetrate the septum to access the reservoir therebelow when the needle is aligned with the subcutaneous medical device. In some embodiments, the acoustic signal impinges on the subcutaneous medical device to provide a second reflected signal, different from the first reflected signal, the second reflected signal triggering the LED light to illuminate.

In some embodiments, the first reflected signal is relatively weak or absent relative to the second reflected signal. In some embodiments, the first reflected signal indicates a first distance and the second reflected signal indicates a second distance different from the first distance, the second distance being within a predetermined distance range to indicate the presence of the subcutaneous medical device. The subcutaneous medical device includes a disc of material that provides an increased difference between the first reflected signal and the second reflected signal. The disc of material includes one of platinum, silver, tungsten, gold, cobalt, titanium, silica, or zirconia. The disc is disposed under the reservoir and defines a diameter that extends the same diameter as the reservoir.

These and other features of the concepts provided herein will become more apparent to those of skill in the art in view of the accompanying drawings and following description, which disclose particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A-3C illustrate side views of an access system, in accordance with an embodiment of the present invention.

FIGS. 4A-4C illustrate side views of an access system, in accordance with an embodiment of the present invention.

DETAILED DESCRIPTION OF SELECTED EMBODIMENTS

Figure 1:
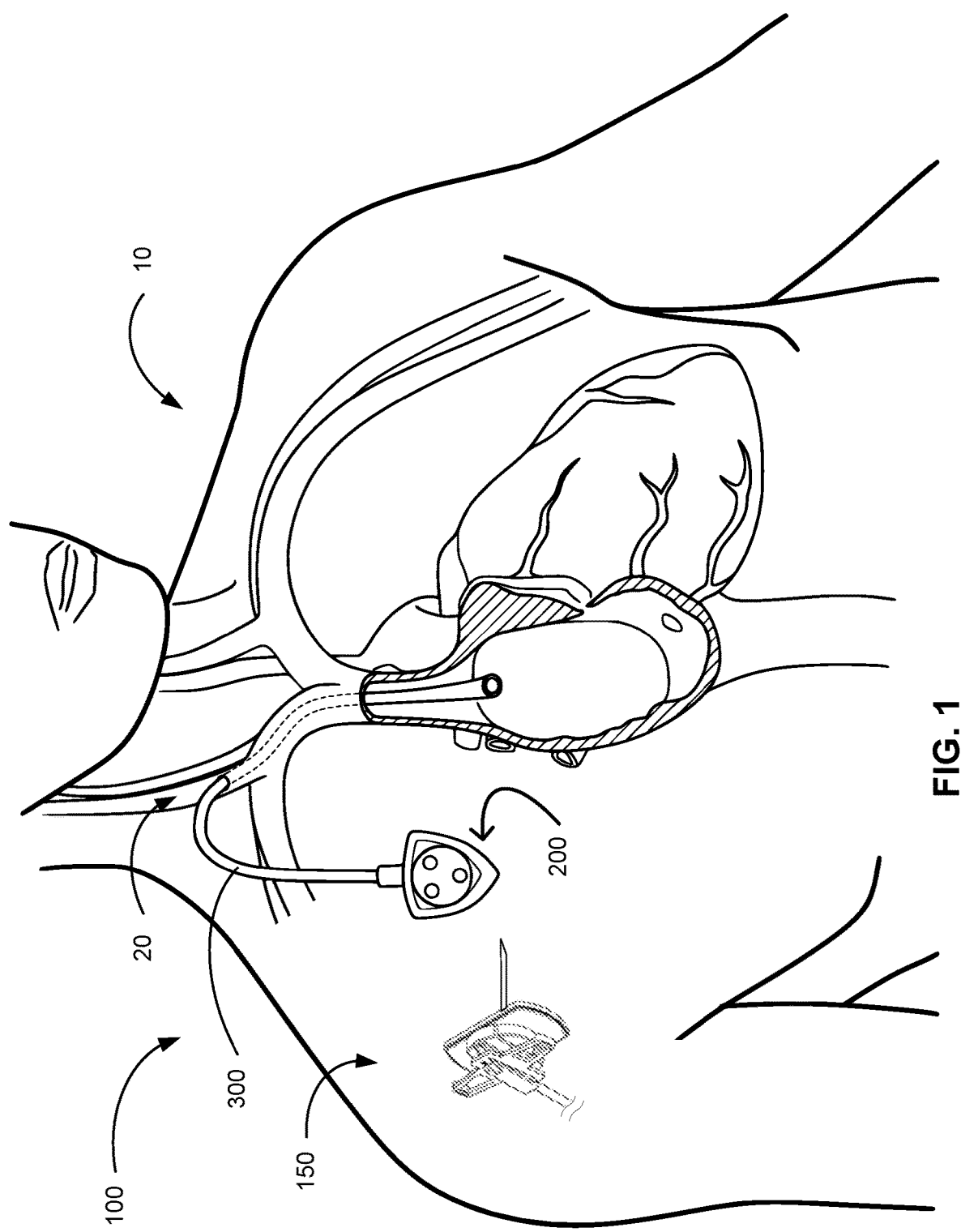
FIG. 1 illustrates an exemplary environment of use for an access system, in accordance with an embodiment of the present invention.

Reference will now be made to figures wherein like structures will be provided with like reference designations. It is understood that the drawings are diagrammatic and schematic representations of exemplary embodiments of the present invention, and are neither limiting nor necessarily drawn to scale. Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

As used herein an "integrated circuit" ("IC"), can include one or more of analog digital or hybrid circuitry, monolithic integrated circuit, silicon chip, semiconductor chip, "chip", "microchip", "555" timers, processors, non-transitory memory, or the like.

Unless defined otherwise, all technical and scientific terms used herein have the same meaning as commonly understood by those of ordinary skill in the art.

Embodiments of the present invention are generally directed to access systems configured to indicate correct alignment with an implanted medical device disposed within the body of a patient to mitigate mis-sticks. An example of such a medical device includes an implantable vascular access port, though a variety of other implantable devices can benefit from use of the present system. Ports, particularly low-profile port septa, can be difficult to find once the ports are implanted under the skin and even harder to align access needles correctly. Accordingly, there is a need for access devices to confirm correct alignment and to mitigate mis-sticks.

FIG. 1 illustrates an exemplary environment of use for the access system 100 according to one embodiment. The access system 100 includes an access device 150, and a subcutaneous medical device, such as a vascular access port ("port") 200. As used herein, a port 200 is used as an exemplary medical device, however it will be appreciated that embodiments of the system 100 can also include other implantable medical devices such as catheters, stents, pumps, combinations thereof, or the like. In addition, port 200 is shown throughout the drawings with certain features, such as septum bumps, suture holes, etc., which are optional. In addition, the port 200 is shown as having a certain shape, which is also optional. It should be appreciated that the access system described herein is possible for any type of vascular access port or other implanted medical device. The port 200 is subcutaneously implanted in a patient 10 with a catheter 300 fluidly connecting the port 200 with a vasculature 20 of the patient 10.

An access device 150 can transcutaneously access the port 200 to deliver medicaments or other fluids to the port 200 and to the vasculature 20 of the patient by way of catheter 300. As used herein, the access device 150 can include any infusion set, extension set, or needle device that can be used to fluidly access the implanted port 200 for the delivery of medicaments or other fluids.

Figure 2B:
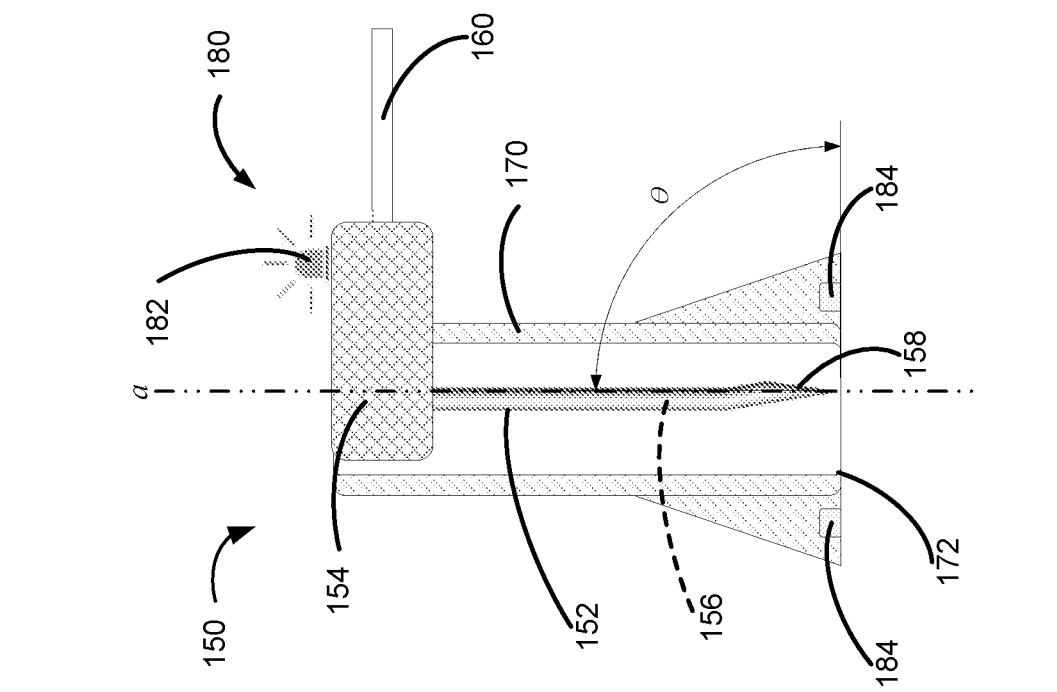
FIG. 2B illustrates a side view of an access assembly, in accordance with an embodiment of the present invention.
Figure 2A:
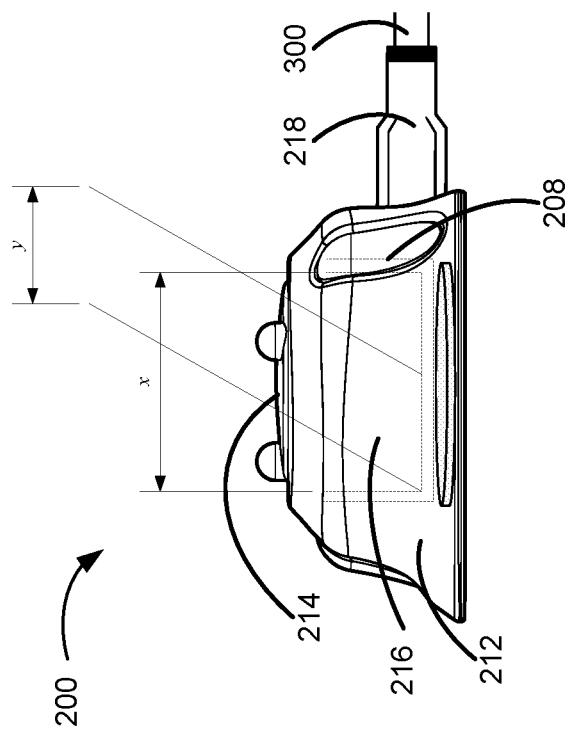
FIG. 2A illustrates a side view of an exemplary implantable medical device, in accordance with an embodiment of the present invention.

FIGS. 2A-2B illustrate further details of the access system 100 for aligning the access device 150 with an implanted medical device 200 (e.g. port), according to one embodiment. As shown in FIG. 2A, the port 200 includes a body 212 and a needle-penetrable septum 214 that cooperates with the body 212 to define a fluid reservoir 216. Optionally, the port body 212 can include suture holes 208. An indwelling catheter 300 is fluidly connected to an outlet 218 of the reservoir 216 of the port 200 so as to enable medicaments or other fluids transcutaneously delivered to the port reservoir 216 via a needle 152 of an access device 150 (via needle piercing of the septum 214) to be delivered to the vasculature 20 of the patient 10.

As shown in FIG. 2B, the access device 150 can include a needle 152 supported by a needle hub 154. The needle 152 can be a non-coring needle, Huber needle, "bendable" needle, or similar needle configured to pierce a skin surface 90 and the port septum 214, to access the reservoir 216 of the subcutaneous port 200. The needle 152 can define a lumen 156 that provides fluid communication between a distal opening 158 disposed adjacent a distal tip of the needle 152 and an extension leg 160 extending from the needle hub 154.

Figures 6A, 6B, 6C:
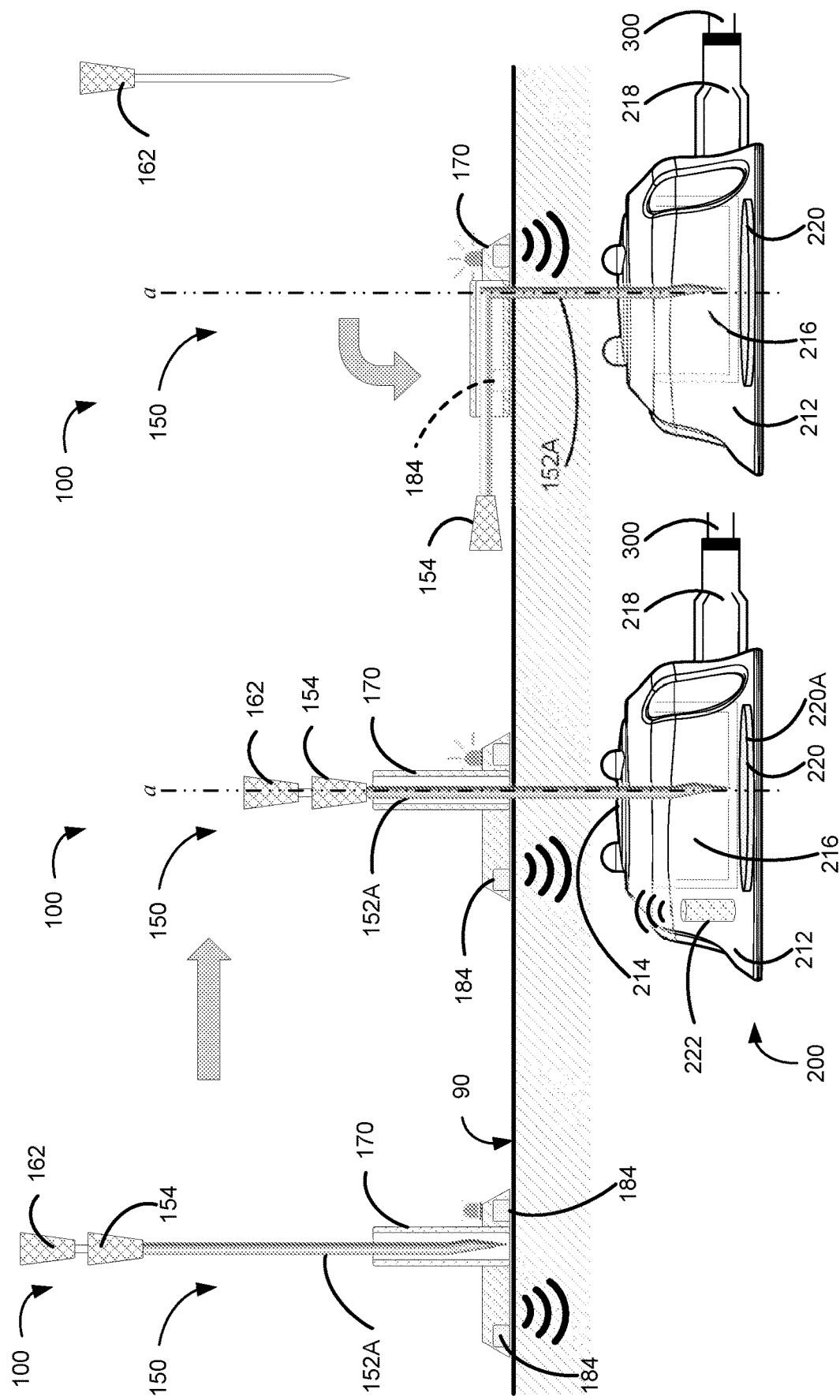
FIGS. 6A-6C illustrate side views of an access system, in accordance with an embodiment of the present invention.

In an embodiment, as shown in FIGS. 6A-6C, the needle 152A can include a "bendable" needle 152A or cannula. The bendable needle 152A can be inserted to access the port 200 as described herein. Once the distal opening 158 is disposed within the reservoir 216, a portion of the needle adjacent the skin surface can be configured to bend such that a proximal portion of the needle disposed outside of the body can lie flat against the skin surface. In an embodiment, a portion of the needle 152A can be heat treated to become malleable to allow the needle to bend. This can contrast with portions of the needle 152A that are not heat treated and remain substantially rigid or inflexible. In an embodiment, a portion of the needle 152A can include a different material or can include a different physical structure (e.g. braid, coil, perforation, or the like) to allow the portion of the needle 152A to bend. In an embodiment, the access device 150 can further include a trocar 162, or similar device disposed within the needle lumen to support the needle during insertion and prevent the bendable portion of the needle from buckling prematurely. Once the needle 152A has been inserted, the trocar 162 can be removed and the needle can be bent to lie flat against the skin surface, as described herein. Advantageously, the "bendable" needle 152A can access ports 200 disposed at different depths below the skin surface, while a remainder of the needle 152A can bend to lie flat against the skin surface.

In an embodiment, the access device 150 can further include a housing 170 configured to support one of the needle 152 or the needle hub 154 and be slidably engaged therewith. The housing 170 can define a bottom surface 172 configured to engage a skin surface 90 of the patient. The bottom surface 172 can align an axis ($\alpha$) of the needle 152 relative to a skin surface 90. In an embodiment, the bottom surface 172 can align an axis of the needle 152 at a predetermined angle (θ) relative to the skin surface 90. The predetermined angle (θ) can be less than or equal to 90° relative to the skin surface 90. Advantageously the predetermined angle (θ) can align the needle distal opening 158 to access the reservoir.

As shown in FIG. 2A, in an embodiment where the predetermined angle (θ) is substantially 90° relative to the skin surface 90, the septum 214 provides the largest possible target window (x) for accessing the reservoir 216, mitigating mis-sticks. Further, the needle 152 can traverse the septum 214 at a minimum vertical distance, prolonging the life of the septum 214. However, where the needle 152 is at an angle of <90° relative to the skin surface the target widow (y) is substantially reduced. As will be appreciated, any inadvertent deviations from a 90° angle by a user without the benefits of embodiments disclosed herein, can dramatically increase the probability of mis-sticks.

In an embodiment, where the predetermined angle (θ) is at an angle <90° relative to the skin surface 90, the needle distal opening 158 can be disposed entirely within the reservoir 216 while requiring a shorter overall vertical height to the reservoir 216, providing a lower overall profile to the port 200. Further details of such ports can be found in WO 2020/028847, filed Aug. 2, 2019, which is incorporated by reference in its entirety into this application. Embodiments described herein can either maintain a 90° angle or where the predetermined angle (θ) is intentionally less than 90°, embodiments can provide increased accuracy for a user, mitigating mis-sticks of low profile ports.

In an embodiment, the needle hub 154 can be slidably engaged with the housing 170 along an axis extending parallel to the axis (α) of the needle 152. As such, the needle hub 154 can transition between a retracted position (FIG. 2B, 3B) and an extended position (FIG. 3C). In the retracted position, a distal tip of the needle 152 is disposed above the bottom surface 172 of the housing 170, such that the needle 152 can be disposed within the housing 170. Advantageously, the needle 152 in the retracted position can mitigate accidental needle stick injuries. In the extended position, the distal tip of the needle 152 can extend below the bottom surface 172 of the housing 170, such that the needle 152 can penetrate a skin surface 90 engaged with the bottom surface 172.

As shown in FIGS. 3A-3C, in use, a clinician can engage the bottom surface 172 of the housing 170 with the skin surface 90 and manipulate the access device 150 until the needle 152 aligns with the target window of the septum 216, disposed subcutaneously therebelow. The clinician can then slide the needle hub 154 from the retracted position (FIG. 3B) to the extended position (FIG. 3C) so that the needle 152 penetrates the port septum 216 and the distal opening 158 accesses the reservoir 216.

As noted herein, locating the port 200 can be performed by palpation of the skin surface of the patient to facilitate aligning the needle 152 with the port septum 216. However, this requires the port 200 and or port septum 216 to be sufficiently large enough in order to be successfully palpated. During placement of such large ports, the skin can be stretched leading to prolonged wound healing, increased scarring, and increased discomfort, which can be detrimental to the patient.

In an embodiment, the access device 150 can include an indicator system 180 configured to indicate to the clinician when the needle 150 is aligned with the target window of the port 200. Advantageously, the indicator system 180 can indicate to the clinician when the needle 150 is aligned with the port 200 without requiring any palpation of the port 200.

Further, the indicator system 180 can provide highly accurate alignment of the needle 152 with the port 200 to allow for smaller, lower profile ports 200, or angled insertions to the ports. These smaller ports can provide improved wound healing, less scarring, and less discomfort to the patient.

Advantageously, the indicator system 180 can be contained within the access device 150, i.e. needle hub 154 and/or housing 170, to provide a convenient indication of correct alignment with the port reservoir 216 at the insertion site. As such, the clinician does not have to divert their attention from the insertion site to confirm alignment. Further, the access device 150 does not require any additional imaging equipment, consoles, monitors, or computing devices coupled thereto, to confirm alignment. This can further reduce the costs required for the additional equipment and expertise in operating such additional equipment.

In an embodiment, the indicator system 180 can include an indicator 182 configured to alert the user when the needle 152 is aligned with the port 200 by one of visual, audible, or tactile alerts. For example, the access device can include an LED indicator 182 configured to illuminate or change color when the needle 152 is correctly aligned. In an embodiment, the LED can project an image or symbol onto a skin surface 90. In an embodiment, the access device 150 can provide a vibration or audible alert when the needle 152 is correctly aligned. In an embodiment, one of the needle hub 154 or housing 170 can be formed of a transparent or translucent material and can refract the light of the LED 182 therethrough.

In an embodiment, the indicator system 180 can include one or more sensors 184 disposed within the access device 150 and configured to detect the presence of the port 200 disposed therebelow. When the presence of the port 200 is detected the indicator system 180 can actuate the indicator to alert the clinician that the axis of the needle 152 is correctly aligned with the port reservoir 216. Optionally, the indicator system 180 can include a power source configured to power the sensor 184, indicator 182, and any associated circuitry.

Figure 5A:
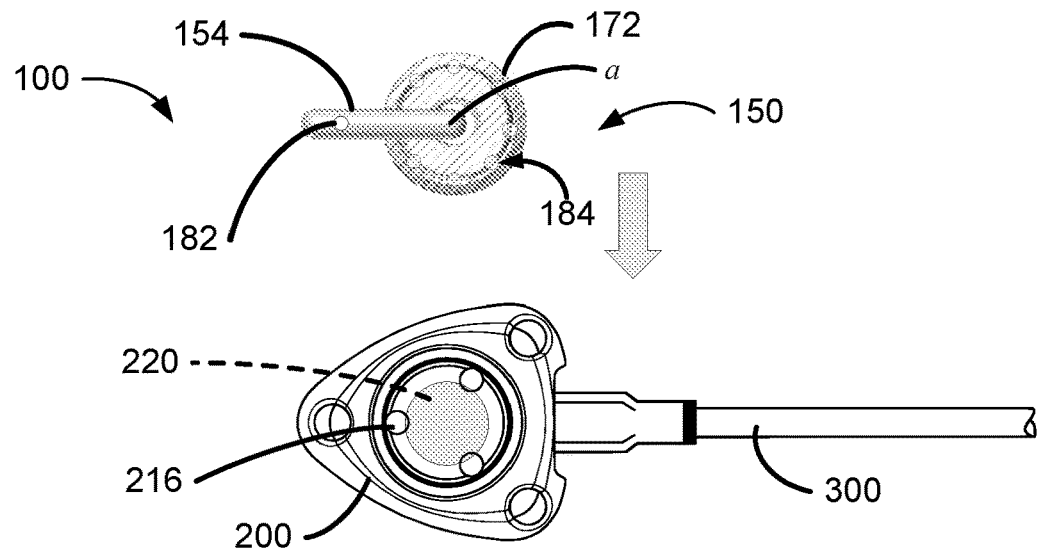
FIGS. 5A-5C illustrate plan views of an access system, in accordance with an embodiment of the present invention.
Figure 5B:
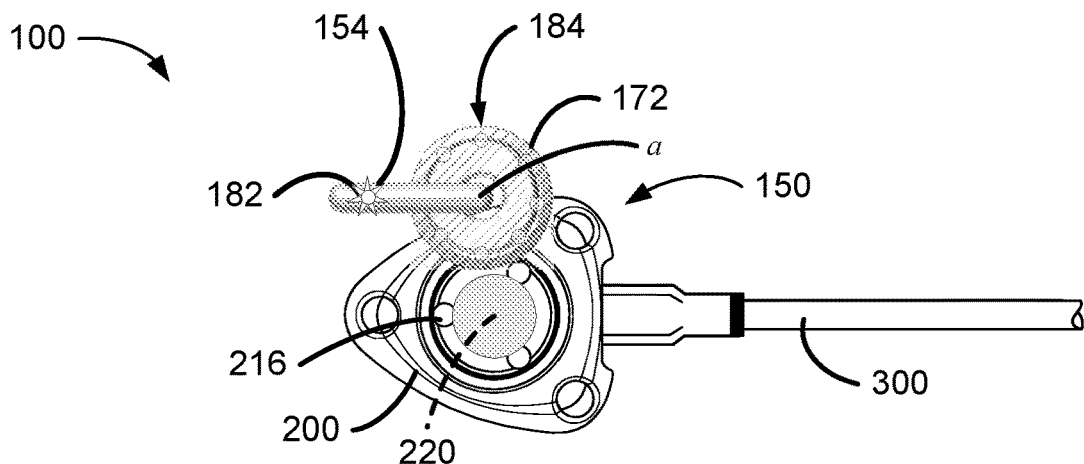
Figure 5C:
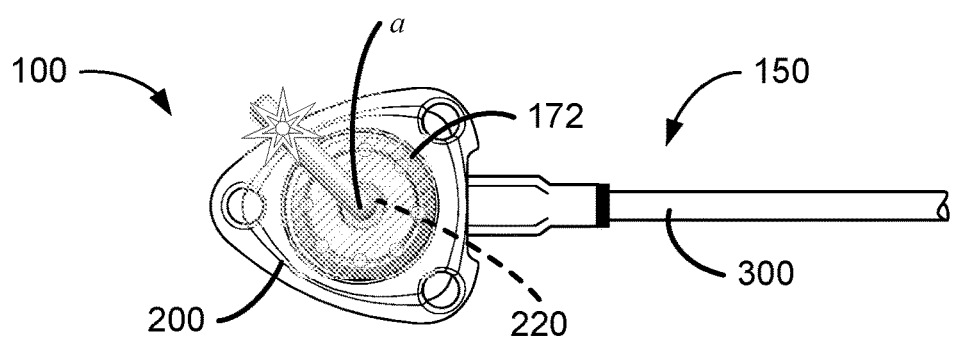

As shown in FIGS. 3A-3C, in an embodiment, the sensor can be disposed in a bottom surface 172 of the housing and configured to contact a skin surface 90. As shown in FIGS. 4A-4C, in an embodiment, the sensor 184 can be disposed in a needle hub 154. In an embodiment, as shown in FIGS. 5A-5C the sensor 184 can be an array of two or more sensors disposed about the axis (α) of the needle 152. In an embodiment, the sensor 184 can define a toroidal shape and is disposed annularly about the axis (α) of the needle 152.

FIGS. 4A-4C show an embodiment of the access device 150 including the indicator system 180 disposed within the needle hub 154. As shown, the access device 150 can be provided without a housing 170. The clinician can guide the access device 150 above the skin surface 90 (FIG. 4A) until the sensor 184 detects that the axis of the needle 152 is correctly aligned with the port reservoir 216 (FIG. 4B). The indicator system 180 can indicate as such by actuating the indicator 182. The clinician can then insert the needle transcutaneously to access the port 200 (FIG. 4C). Advantageously, the access device 150 of FIGS. 4A-4C including the indicator system 180, provide little or no increase in overall size of the access device 150 relative to a needle and needle hub assembly alone. As such, the clinician can access smaller, lower profile ports while mitigating mis-stick attempts without any additional monitors, computing devices, or the like, and can maintain their attention at the insertion site.

FIGS. 5A-5C shown plan views of an embodiment of an access system 100. As shown in FIG. 5A, the access device 150 is not aligned with a target window of the septum 216. The sensor 184 fails to detect the port disposed therebelow and the indicator 182 is not actuated. As shown in FIGS. 5B-5C, by sliding the access device 150 over the surface of the skin 90 towards the location of the port 200, the sensor 184 can detect when the axis of the needle 152 is sufficiently aligned with the septum 216 to access the reservoir therebelow. The sensor 184 can detect the presence of the port 200 disposed subcutaneously and alert the clinician when the needle is sufficiently aligned with the port reservoir 216, by actuating the indicator 182 (FIG. 5C).

In an embodiment, the indicator system 180 can detect the presence of the port 200 by way of one or more modalities. Exemplary modalities can include capacitance, induction, magnetic, thermal, acoustic, radio frequency (RF), combinations thereof, or the like, as described in more detail herein.

Capacitance Modality

In an embodiment, the indicator system 180 can employ a capacitance modality and include a capacitance sensor plate 184 and associated circuitry configured to detect a change in the dielectric constant of the tissues disposed below the bottom surface 172 of the access device 150.

For example, as shown in FIG. 3A the capacitance of the skin surface tissues can provide a first dielectric constant reading. As shown in FIG. 3B, the capacitance of the port 200 disposed subcutaneously, can provide a second dielectric constant reading different from the first dielectric constant reading. The indicator system 180 can detect the change in capacitance of the tissues disposed therebelow and indicate, e.g. by illuminating the LED 182, that the needle 152 is aligned with the port septum 214 and reservoir 216. As shown in FIG. 3C, the clinician can slide the needle hub 154 from the retracted position to the extended position to access the port 200. The range of the capacitance modality sensor 184 can be between 0.15 inch and 3 inch below the skin surface. Although greater or lesser ranges are also contemplated. Advantageously, the capacitance modality of the indicator system 180 can detect the presence of port 200 without requiring the port 200 to provide any active signal or returned signal. As such the access device 150 can be used with various subcutaneous medical devices that do not require any specific adaptations.

In an embodiment, the port 200, or a portion thereof, can include a material that provides a different capacitance relative to the surrounding tissues or a different dielectric constant relative to the surrounding materials. For example, the port body 212, or portion thereof (e.g. disc 220), can include a material such as platinum, silver, tungsten, gold, cobalt, titanium, silica, zirconia material, or similar material that provides an increased difference in capacitance or dielectric constant relative to the surrounding materials. In an embodiment, the disc 220 of material can provide an increase in density relative to the material(s) forming the port 200 or the surrounding tissues. In an embodiment, the portion of material, e.g. disc 220, can be positioned below the reservoir 216 or form a reservoir base, and can indicate a target window (e.g. target window (x)) of the reservoir 216 (see FIGS. 5A-5C). Worded differently, the diameter of the disc 220 can substantially align with the diameter of the reservoir 216. The change in capacitance between the surrounding tissues and the port body 212 that includes the disc 220, can provide a clear indication of the presence of the port 200 and improve alignment of the needle 152 with the port 200.

Induction Modality

In an embodiment, the indicator system 180 can include an induction coil 222 disposed within the port body 212. The induction coil 222 can induce a current within the voltmeter sensor 184 disposed within the access device 150 that in turn can cause the LED indicator 182 to illuminate. The strength of the induction coil 222 can be configured to induce a current within a predetermined range of the port or a predetermined direction from the port. Exemplary ranges can be between 0.15 inch and 3 inch. Although greater or lesser ranges are also contemplated. Further, the induction coil 222 can be aligned to induce a current along an axis that extends perpendicular to the skin surface 90. As such, the induction coil 222 can induce a current within the voltmeter sensor 184 when the access device is disposed directly over the port reservoir 216 (e.g. FIG. 3B). When the access device 150 is not aligned with the port reservoir, the voltmeter sensor 184 is out of range of the induction coil 222, no current is induced and the LED indicator 182 does not illuminate.

Advantageously, the LED 182, voltmeter sensor 184, and associated circuitry provide a compact indicator system 180 since access device 150 does not require a power source. Instead, power is provided by the induction coil 222 disposed within the port 200. As such, the induction indicator system 180 can be included within the access device 150 with little or no increase in overall size of comparable access devices 150 that do not include an indicator system 180.

In an embodiment, the voltmeter sensor 184 can include a coil. The induction coil 222 disposed in the port 200 can draw a voltage from the coil disposed in the voltmeter sensor 184, when the needle 152 is aligned with the port 200. The voltmeter can then detect a voltage drop in the coil disposed within the voltmeter 184 to confirm the induction coil 222 is within range, i.e. disposed below the voltmeter sensor 184 and thereby the axis (α) of the needle 152 is aligned with the port reservoir 216. The indicator system 180 can then alert the user by illuminating the LED, as described herein.

In an embodiment, the indicator system 180 can include one or more integrated circuits ("IC"), or the like, configured to detect predetermined voltage set points received from the sensor 184 and provide predetermined outputs to one or more visual, audible, or tactile indicators, such as LED 182 or the like. For example, as shown in FIGS. 5A-5C, the system 100 can include circuitry such as a "555" timer configured to detect a first voltage input to indicate a first proximity to the port 200 and provide a first output of a first rate of flashing LED light 182. As the access device 150 is moved closer to the port 200, and thereby more in line with the reservoir 216, subsequent voltage readings, e.g. a second voltage reading or a third voltage reading, can indicate progressively improved alignment of the needle 152 with the port reservoir 216. As such, the IC or "555" timer can provide a second rate of flashing of the LED 182, that is faster than the first rate, and a third rate of flashing, that is greater than the second rate, until the needle 152 is aligned with the port reservoir 216.

In an embodiment, the different voltage readings from the sensor 184 can be provided by an increase strength of signal detected by the sensor 184. In an embodiment, the different voltage readings can be provided by different numbers of sensors within a sensor array 184 detecting the presence or absence of the port 200 disposed therebelow. For example, as shown in FIGS. 5A-5C, two or more sensors of a sensor array 184 can be disposed annularly about the axis of the needle 152. As shown in FIG. 5B, as an edge of the port 200 is disposed below a first sensor of the sensor array 184 a first voltage reading can be provided indicating that the port is proximate, but not correctly aligned with the access device 150. As shown in FIG. 5C, where all the sensors of the sensor array 184 detect the presence of the port 200, a second voltage reading, different from the first voltage reading is provided indicating the port 200 is correctly aligned with the needle 152.

As will be appreciated, this is exemplary and the IC or "555" timer can provide other modalities of indicator system 180, or other indicators such as a change in LED color, audible signal such as rate of signals, pitch, frequency, amplitude, or rate, frequency or amplitude of vibration signals. These and other configurations of modalities or indicator signal are contemplated to fall within the scope of the present invention.

Magnetic Modality

In an embodiment, the indicator system 180 can employ a magnetic modality. The port 200 can include a portion, e.g. disc 200, including a ferrous or magnetic material that provides a passive magnetic field strength. The sensor 184 can include a magnetic, or "Hall effect" sensor configured to detect the difference in magnetic field strengths between the surrounding tissues, and the port 200 including the disc 220. As the access device 150 is aligned with the port 200, the magnetic field strength can indicate when the port reservoir 216 is aligned beneath the needle 152, as described herein. The user can then manipulate the needle hub 154 to access the port reservoir 216.

Thermal Modality

In an embodiment, the indicator system 180 can employ a thermal modality and include a thermal sensor 184 and associated circuitry configured to detect a change in temperature of the tissues disposed below the access device 150. As shown in FIG. 3A, the temperature of the skin surface tissues can provide a first temperature. As shown in FIG. 3B, the port 200 that is disposed subcutaneously can provide a different temperature from the surrounding tissues, e.g. at FIG. 3B. The indicator system 180 can detect the change in temperature and indicate, e.g. by illuminating the LED 182, that the needle 152 is aligned with the port septum 214 and reservoir 216 disposed therebelow. As shown in FIG. 3C, the clinician can slide the needle hub 154 from the retracted position to the extended position to access the port 200. The range of the temperature modality sensor 184 can be between 0.15 inch and 3 inch. Although greater or lesser ranges are also contemplated. Advantageously, the surface contact temperature sensor 184 can provide a precise window of temperature detection disposed below the access device 150 to provide an accurate alignment of the needle with the port reservoir 216.

Acoustic Modality

In an embodiment, the indicator system 180 can employ an acoustic modality and include an acoustic transducer and sensor 184, and associated circuitry, configured to emit an acoustic, e.g. ultrasonic, signal into the tissues disposed below the access device 150. Further, the acoustic sensor 184 can detect a reflected acoustic signal from the tissues disposed below the access device 150.

As shown in FIG. 3A, the transducer sensor 184 can provide an acoustic signal directed into the tissues directly below the access device 150. The skin surface tissues can provide a first reflected acoustic signal. As shown in FIG. 3B, as the access device 150 is aligned with the port reservoir 216, the emitted acoustic signal reflects off of the port 200 disposed subcutaneously, to provide a second reflected acoustic signal different from the first reflected acoustic signal.

In an embodiment, the first reflected signal can be a relatively weak or absent signal relative to the second reflected signal. As such, the transducer sensor 184 can detect the port 200 due to the presence of the second reflected signal or an increase in strength of the second reflected signal compared with the first reflected signal.

In an embodiment, the first reflected signal can detect a first subcutaneous object, e.g. bone, or the like, at a first distance calculated from the time elapsed between the emitted signal and the reflected signal. The second reflected signal can detect a second subcutaneous object, e.g. port 200, at a second distance, which is less than the first distance or is within a predetermined range. As such, if the second reflected signal is within the predetermined range, the presence of the port 200 is confirmed. In an embodiment the predetermined range of the acoustic signal can be between 0.15 inch and 3 inch, although greater or lesser ranges are also contemplated.

The indicator system 180 can detect the reflected acoustic signal and determine the presence of the port 200 disposed therebelow. The indicator system 180 can then alert the user, e.g. by illuminating an LED 182, that the needle 152 is aligned with the port septum 214 and reservoir 216 disposed therebelow. As shown in FIG. 3C, the clinician can then slide the needle hub 154 from the retracted position to the extended position to access the port 200. In an embodiment, the acoustic modality of the indicator system 180 can detect the presence of port 200 without requiring the port 200 to provide any active signal. As such the acoustic modality access device 150 can be used with various subcutaneous medical devices that do not require any specific adaptations.

In an embodiment, the port 200, or a portion thereof, can include a material that provides different acoustic reflection properties relative to the surrounding tissues. For example, the port 200 can include a disc 220 of material, as described herein, disposed within the port body 212 and below the reservoir 216. The change in acoustic reflective properties between the surrounding tissues and the port body 212 including the disc 220 can provide a clear indication of the presence of the port 200 and the alignment with the needle 152. In an embodiment, the disc 220 of material can provide an increase in density relative to the material(s) forming the port 200 or the surrounding tissues. In an embodiment, the disc 220 can include one of platinum, silver, tungsten, gold, cobalt, titanium, silica, or zirconia. However, other materials with different acoustic properties are also contemplated.

RFID Modality

In an embodiment, the indicator system 180 can employ a radio frequency (RF) modality and include an RFID emitter and sensor 184, and associated circuitry configured to emit an RF signal into the tissues disposed below the access device 150 and detect a reflected RFID signal from the tissues disposed below the access device 150.

As shown in FIG. 3A, the RFID emitter and sensor 184 can provide an RF signal directed into the tissues directly below the access device 150. With the absence of any port 200 and associated RFID tag 220A disposed therebelow, no reflected signal is provided, indicating the needle 152 is not aligned with the port reservoir 216. As shown in FIG. 3B, as the access device 150 is aligned with the port reservoir 216, the emitted RFID signal from the sensor 184 reflects off of the RFID tag 220A disposed within the port 200 disposed subcutaneously, to provide a reflected response signal different. The transducer sensor 184 of the indicator system 180 can detect the reflected response signal and indicate, e.g. by illuminating the LED 182, that the needle 152 is aligned with the port septum 214 and reservoir 216 disposed therebelow. As shown in FIG. 3C, the clinician can then slide the needle hub 154 from the retracted position to the extended position to access the port 200. The distance range of the emitted RFID signal from the RFID emitter and sensor 184 can penetrate the skin surface tissues to a depth of between 0.15 inch and 3 inch. Although greater or lesser ranges are also contemplated Advantageously, the RFID reflected signal can provide a specific response signal from the port 200 and mitigate the presence of false positives. This can improve the accuracy of detecting and aligning the access device 150 with the port reservoir 216 mitigating mis-sticks. Further, the RFID tag 220A disposed within the port 220 does not require any additional power source in order to provide a response signal. Instead the power to provide the response signal is obtained from the energy of the emitted RFID signal provided by the RFID emitter sensor 184 of the access device 150.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An access assembly configured for detecting and accessing a subcutaneous medical device, the access assembly comprising:
   a needle supported by a needle hub; and
   an indicator system comprising:
      a capacitance sensor configured to detect a change in a dielectric constant between the subcutaneous medical device and a surrounding tissue; and
      an LED light configured to indicate when the needle is aligned with the subcutaneous medical device.

2. The access assembly according to claim 1, further including a housing supporting the needle hub and slidably engaged therewith, the needle hub configured to transition between a retracted position and an extended position, the housing defining a bottom surface configured to engage a skin surface, the capacitance sensor disposed in the bottom surface.

3. The access assembly according to claim 2, wherein the LED light is disposed on one of the housing or the needle hub.

4. The access assembly according to claim 1, wherein the subcutaneous medical device is a port including a port body and a septum co-operating to define a reservoir, the needle configured to penetrate the septum to access the reservoir therebelow when the needle is aligned with the subcutaneous medical device.

5. The access assembly according to claim 1, wherein the subcutaneous medical device includes a disc of material that provides an increased difference in the dielectric constant from the surrounding tissue.

6. The access assembly according to claim 5, wherein the disc of material includes one of platinum, silver, tungsten, gold, cobalt, titanium, silica, or zirconia.

7. The access assembly according to claim 5, wherein the disc is disposed under a reservoir and defines a diameter that extends a same diameter as the reservoir.

8. The access assembly according to claim 1, wherein the capacitance sensor can detect a change in dielectric constant to a depth of between 0.15 inch and 3 inch below a skin surface.

* * * * *